(12) United States Patent
Kawamoto et al.

(10) Patent No.: US 10,791,942 B2
(45) Date of Patent: Oct. 6, 2020

(54) PULSE WAVE ANALYZING APPARATUS

(71) Applicants: HIROSHIMA UNIVERSITY, Higashi-Hiroshima-shi, Hiroshima (JP); NIHON KOHDEN CORPORATION, Shinjuku-ku, Tokyo (JP)

(72) Inventors: Masashi Kawamoto, Hiroshima (JP); Noboru Saeki, Hiroshima (JP); Ryuji Nakamura, Hiroshima (JP); Teiji Ukawa, Tokyo (JP); Tsuneo Takayanagi, Tokyo (JP); Haruka Morimoto, Tokyo (JP)

(73) Assignees: HIROSHIMA UNIVERSITY, Hiroshima (JP); NIHON KOHDEN CORPORATION, Tokyo (JP)

(*) Notice: Subject to any disclaimer, the term of this patent is extended or adjusted under 35 U.S.C. 154(b) by 150 days.

(21) Appl. No.: 15/511,117

(22) PCT Filed: Dec. 3, 2015

(86) PCT No.: PCT/JP2015/006014
§ 371 (c)(1),
(2) Date: Mar. 14, 2017

(87) PCT Pub. No.: WO2016/092784
PCT Pub. Date: Jun. 16, 2016

(65) Prior Publication Data
US 2017/0273582 A1    Sep. 28, 2017

(30) Foreign Application Priority Data
Dec. 11, 2014 (JP) .................. 2014-251022

(51) Int. Cl.
A61B 5/02 (2006.01)
A61B 5/024 (2006.01)
(Continued)

(52) U.S. Cl.
CPC ........ *A61B 5/02444* (2013.01); *A61B 5/0205* (2013.01); *A61B 5/02108* (2013.01);
(Continued)

(58) Field of Classification Search
CPC ............ A61B 5/02444; A61B 5/02116; A61B 5/0205; A61B 5/7257; A61B 5/02108; A61B 2562/02
See application file for complete search history.

(56) References Cited

U.S. PATENT DOCUMENTS 5,385,149 A    1/1995 Chang et al.
5,776,070 A    7/1998 Kitazawa et al.
(Continued)

FOREIGN PATENT DOCUMENTS

CN    102499650 A    6/2012
EP    0 925 757 A1    6/1999
(Continued)

OTHER PUBLICATIONS

International Search Report Issued in Patent Application No. PCT/JP2015/006014 dated Feb. 15, 2016.
(Continued)

*Primary Examiner* — Eric F Winakur
*Assistant Examiner* — David Joseph Fernandez-Fidalgo
(74) *Attorney, Agent, or Firm* — Pearne & Gordon LLP

(57) ABSTRACT

A pulse wave analyzing apparatus comprises an acquiring section (11) which acquires a pulse wave that is non-invasively measured, and an analyzer (12) which calculates data on the frequency axis by using the pulse wave, and which obtains the index value of the respiratory-induced variation based on the calculated data on the frequency axis.

11 Claims, 14 Drawing Sheets

(51) Int. Cl.
  *A61B 5/0205* (2006.01)
  *A61B 5/021* (2006.01)
  *A61B 5/00* (2006.01)

(52) U.S. Cl.
  CPC ........ *A61B 5/02116* (2013.01); *A61B 5/7257* (2013.01); *A61B 2562/02* (2013.01)

(56) References Cited

U.S. PATENT DOCUMENTS

| | | | |
|---|---|---|---|
| 6,099,478 A | 8/2000 | Aoshima et al. | |
| 2002/0133083 A1* | 9/2002 | Ito | A61B 5/0225 600/493 |
| 2004/0260186 A1* | 12/2004 | Dekker | A61B 5/0205 600/483 |
| 2007/0021673 A1* | 1/2007 | Arbel | A61B 5/02 600/500 |
| 2008/0033306 A1 | 2/2008 | Joeken | |
| 2008/0045844 A1 | 2/2008 | Arbel et al. | |
| 2008/0188765 A1 | 8/2008 | Stolarski et al. | |
| 2009/0203972 A1* | 8/2009 | Heneghan | A61B 5/0507 600/301 |
| 2011/0183757 A1 | 7/2011 | Furuta et al. | |

FOREIGN PATENT DOCUMENTS

| | | |
|---|---|---|
| EP | 1 240 867 A2 | 9/2002 |
| EP | 1 884 189 A1 | 2/2008 |
| JP | 2008-237882 A | 10/2008 |

OTHER PUBLICATIONS

Written Opinion Issued in Patent Application No. PCT/JP2015/006014 dated Feb. 15, 2016.
European Office action issued in Patent Application No. EP 15 810 701 dated Mar. 19, 2018.
European Office Action issued in Patent Application No. EP 15 810 701 dated Oct. 18, 2018.
Japanese Office action issued in Patent Application No. JP-2014-251022 dated Nov. 27, 2018.
European Patent Office Communication pursuant to Article 94(3) EPC issued in Patent Application No. EP 15 810 701.1 dated May 17, 2019.
Chinese Office action issued in Chinese Patent Application No. 201580067562 dated May 28, 2019.
European Patent Office Summons to Attend Oral Proceedings Pursuant to Rule 115(1) EPC dated Dec. 5, 2019.

\* cited by examiner

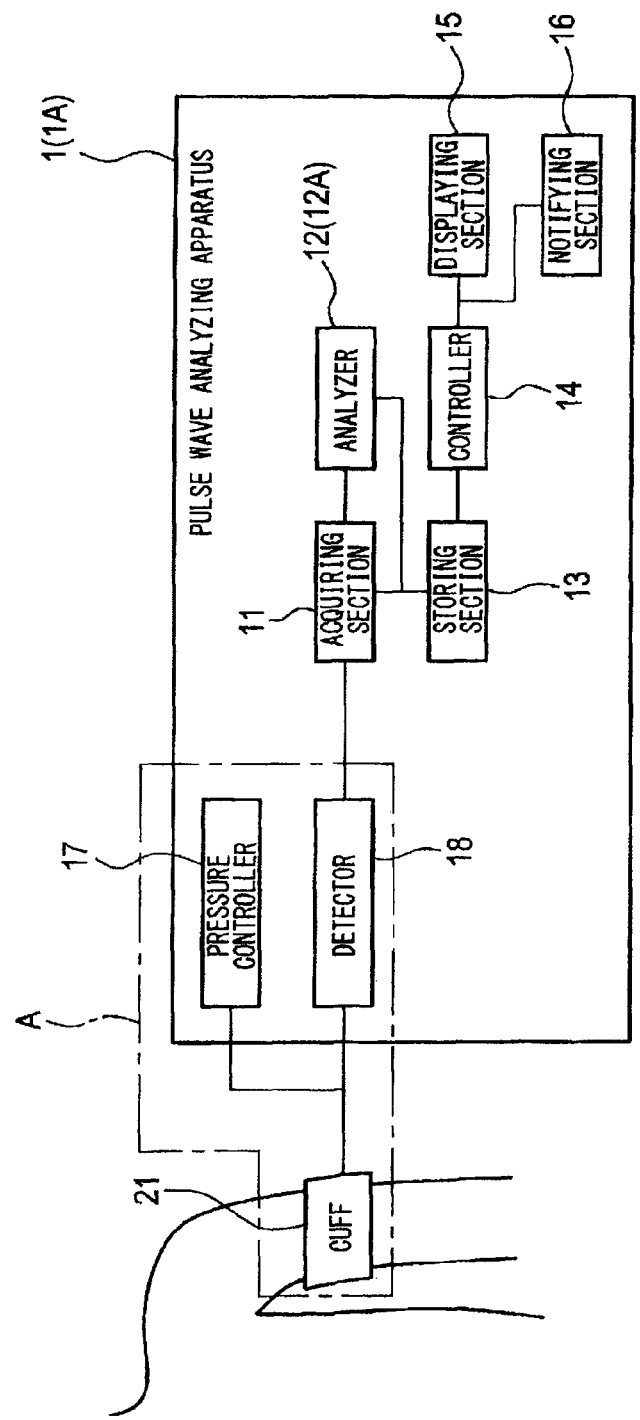
[Fig. 1]

[Fig. 2]
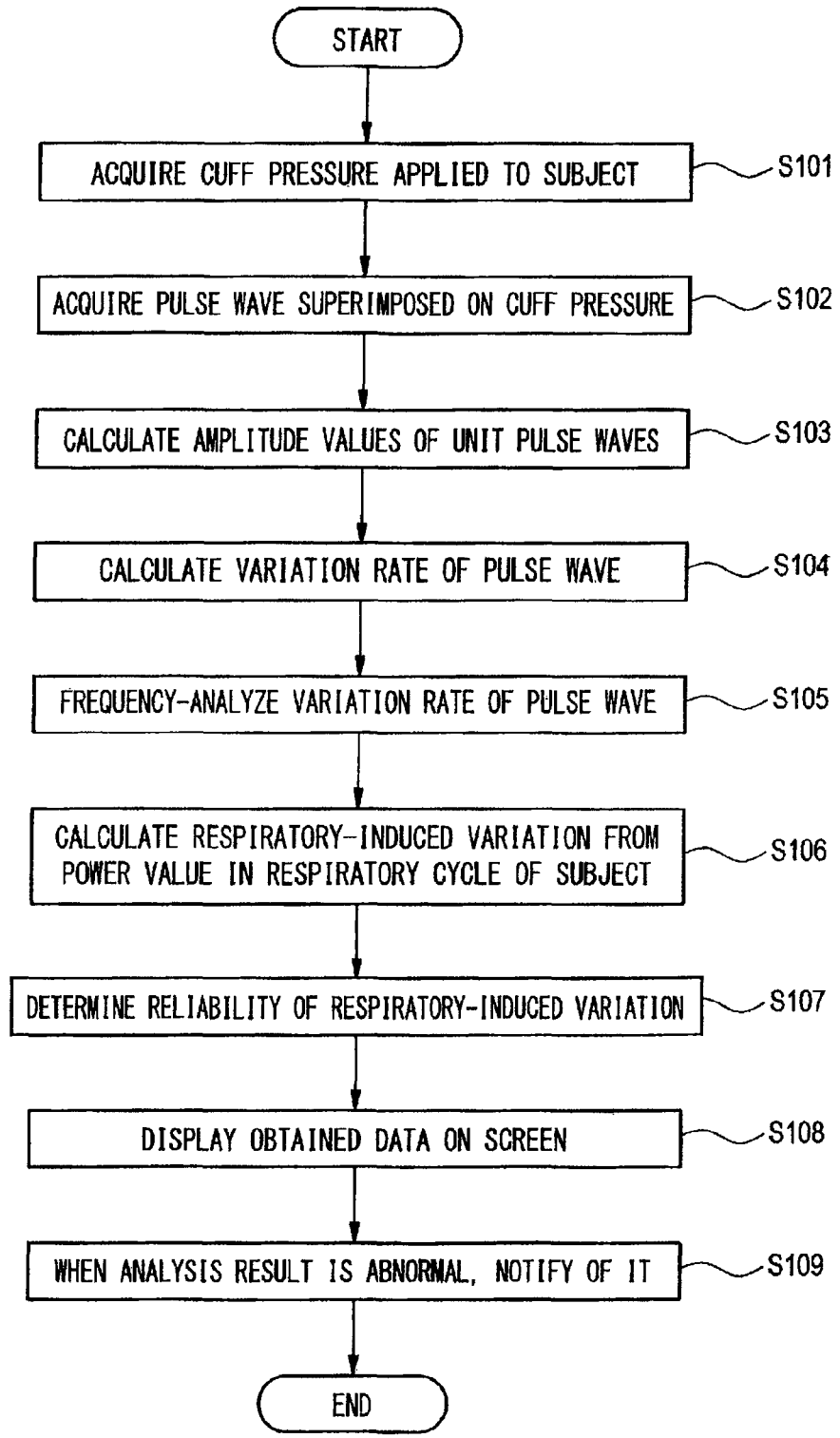

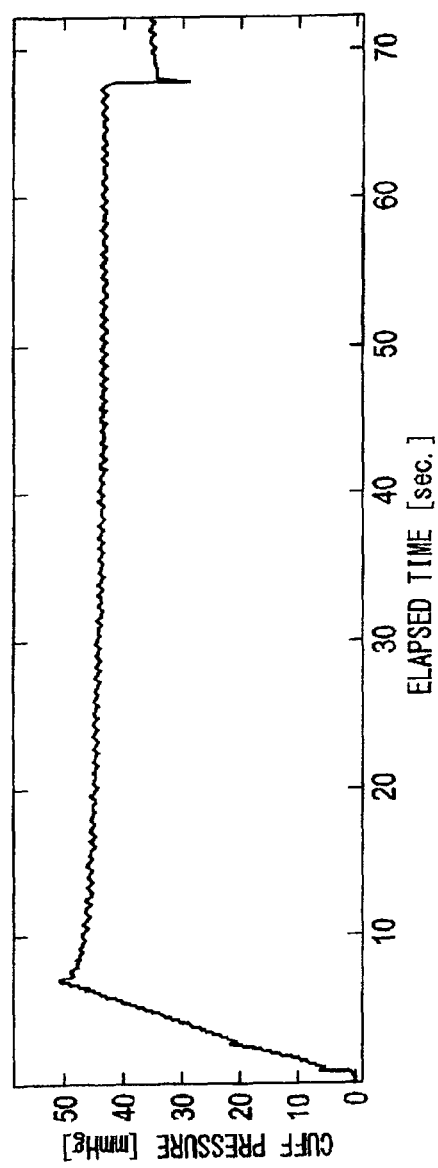
[Fig. 3A]

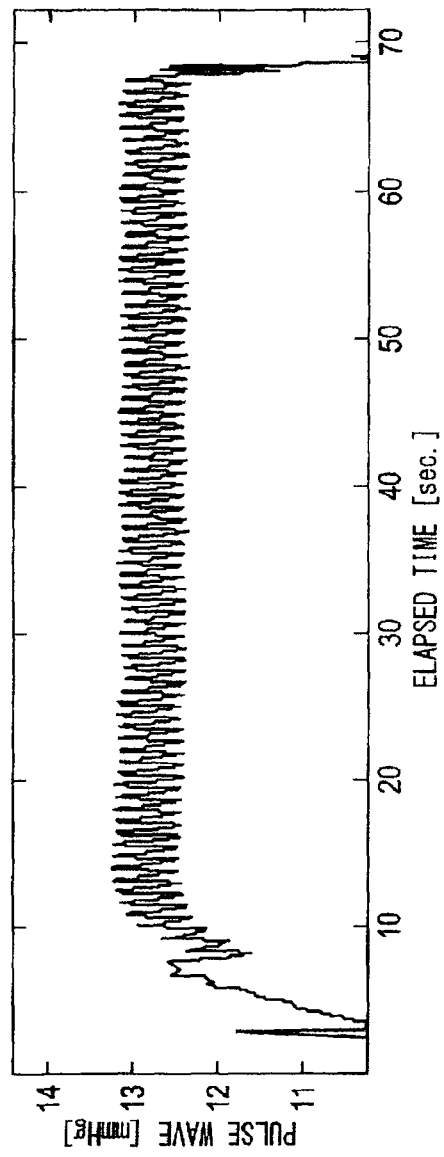
[Fig. 3B]

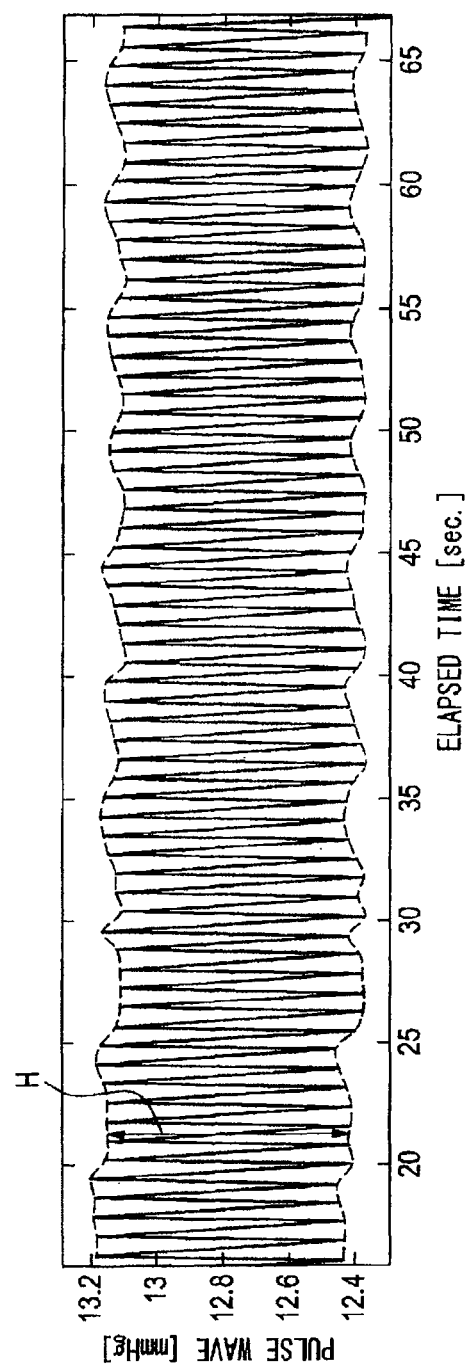
[Fig. 4A]

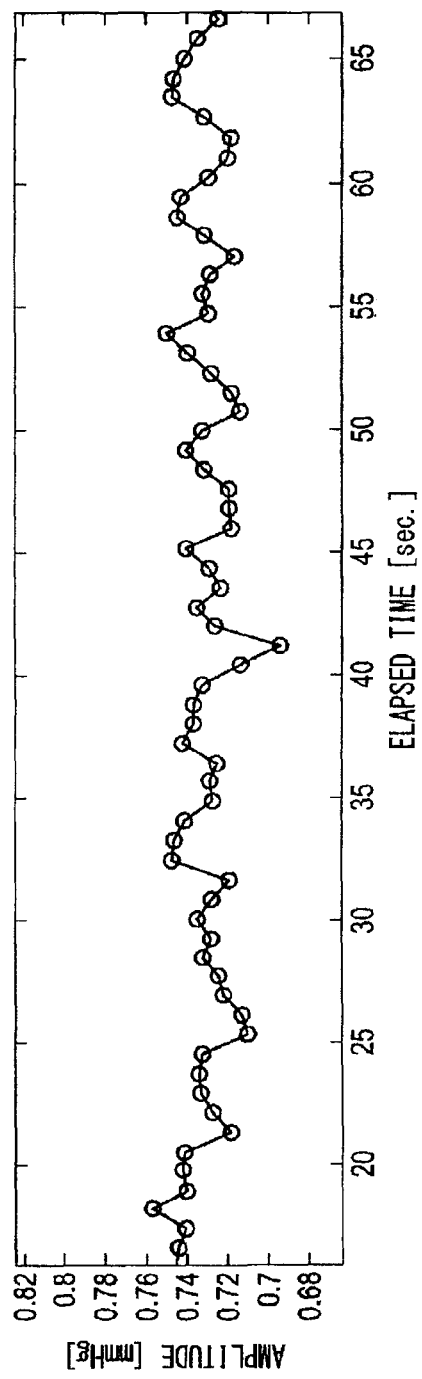
[Fig. 4B]

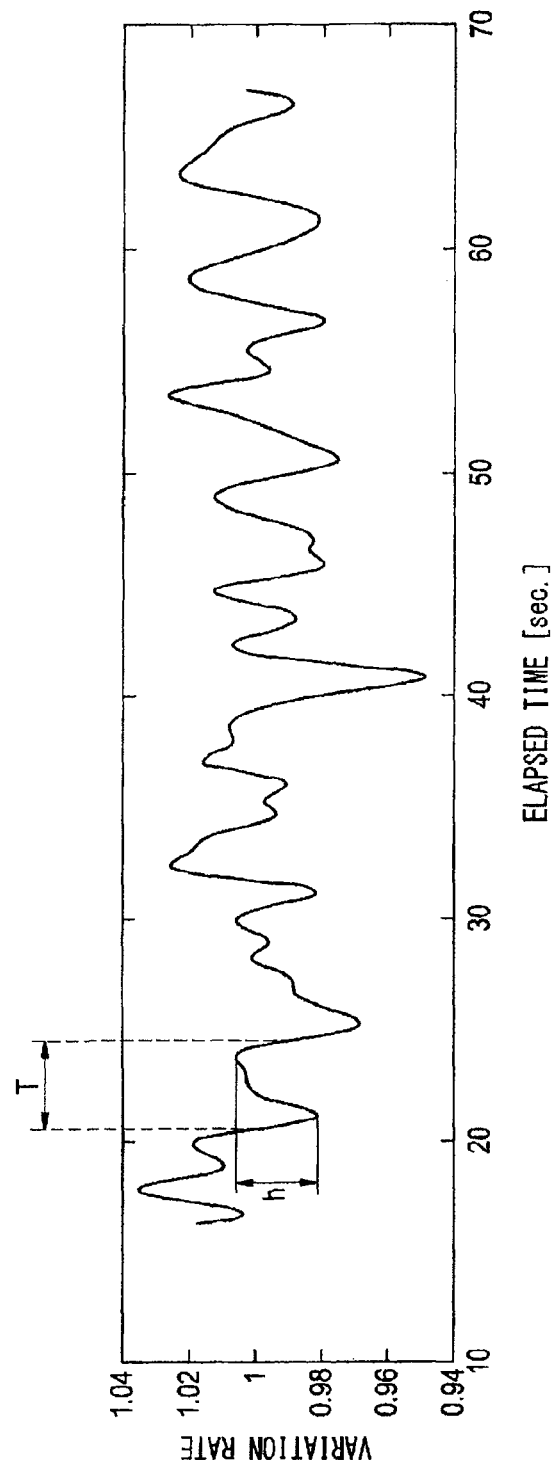
[Fig. 5A]

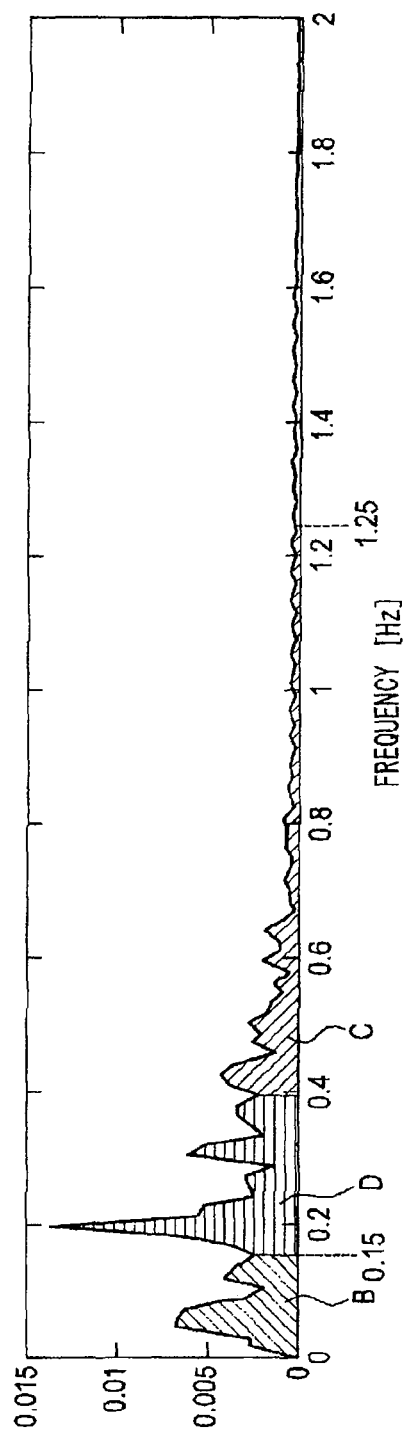
[Fig. 5B]

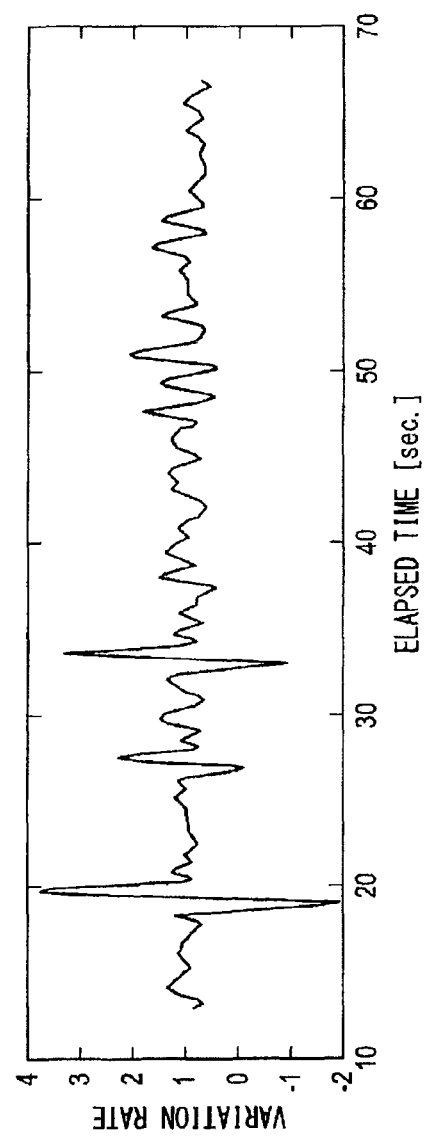
[Fig. 6A]

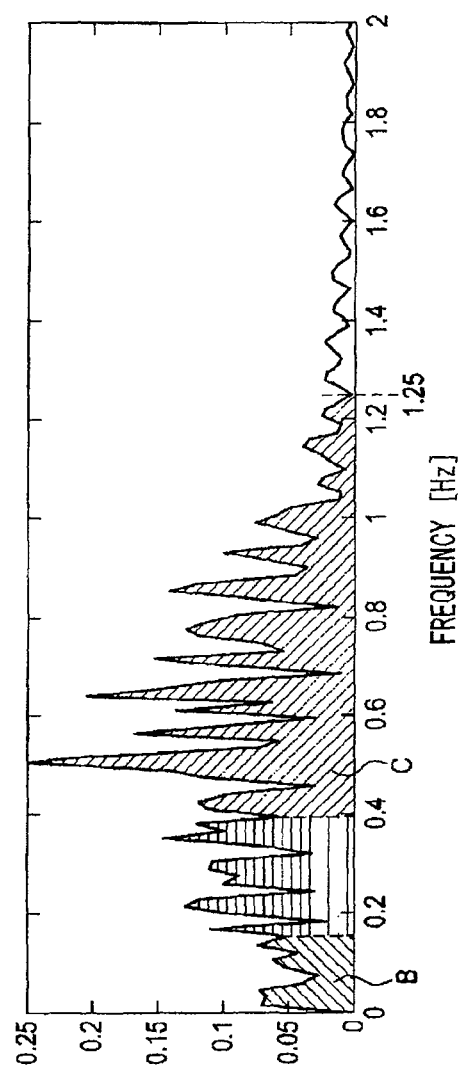
[Fig. 6B]

[Fig. 7]
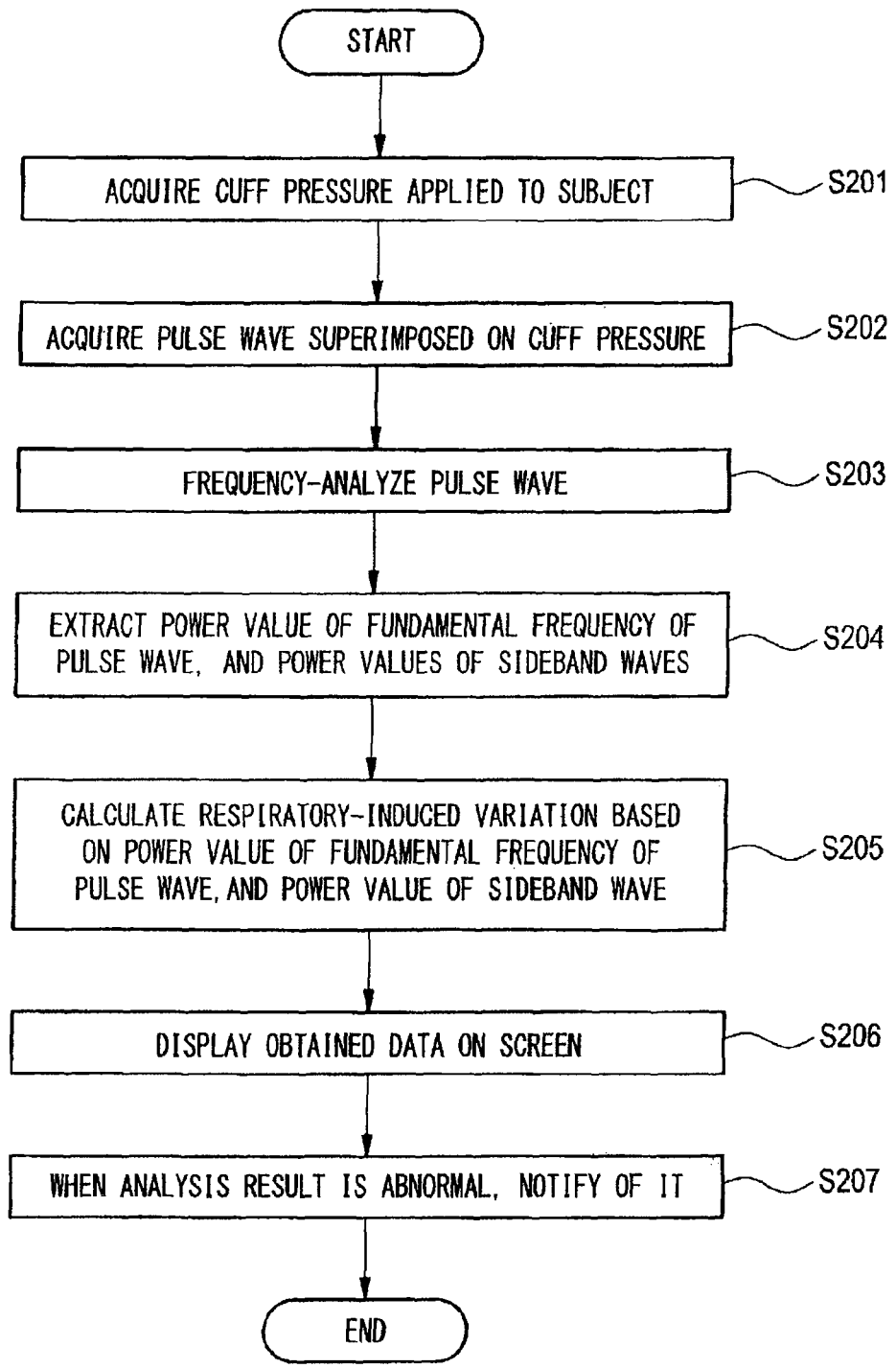

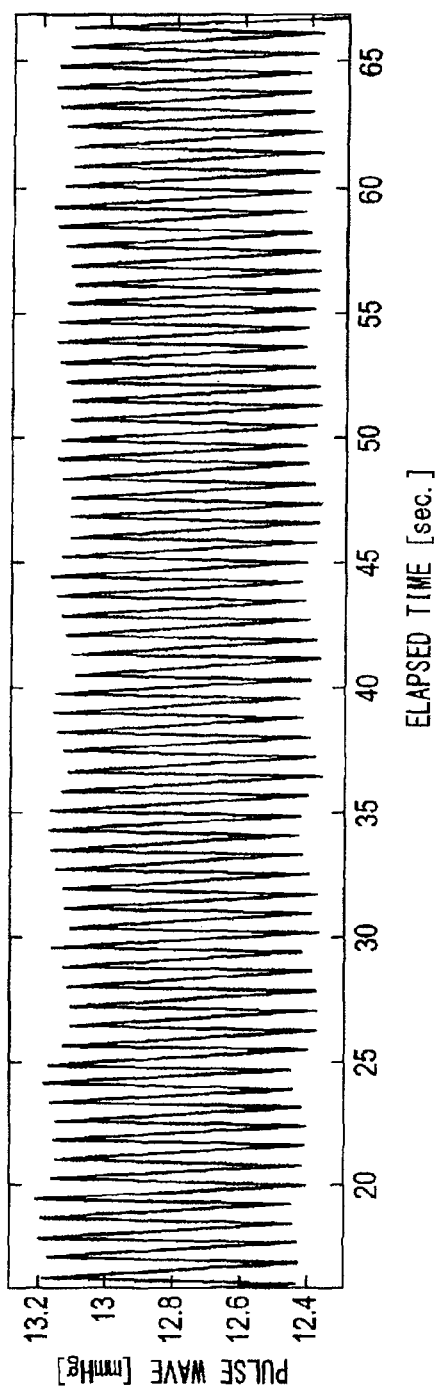
[Fig. 8A]

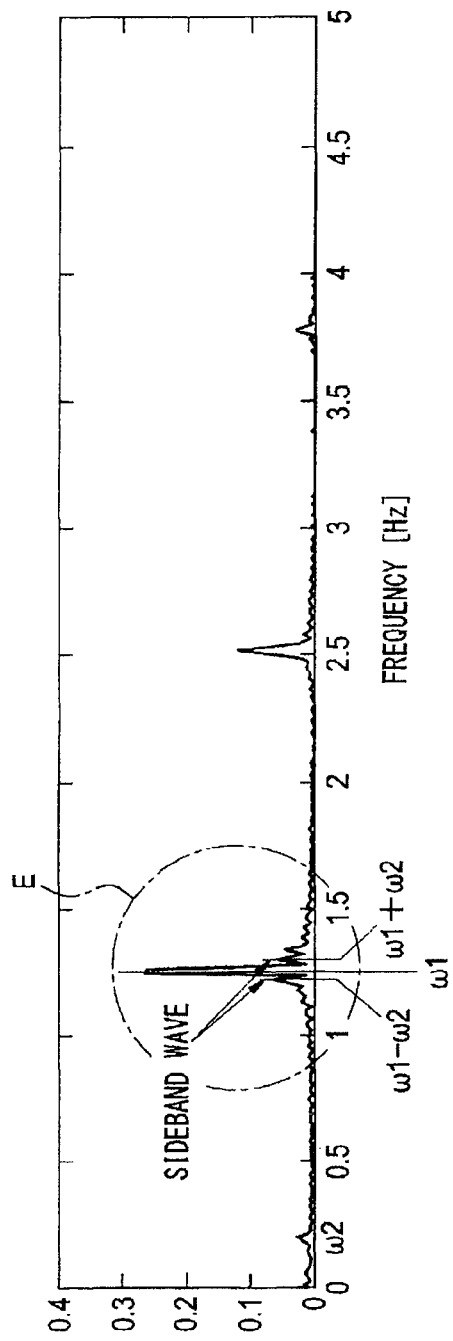
[Fig. 8B]

[Fig. 9A]
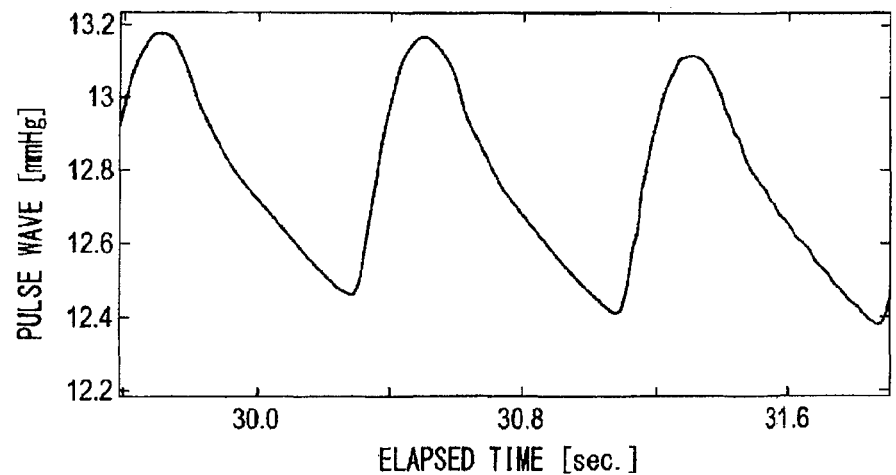
[Fig. 9B]
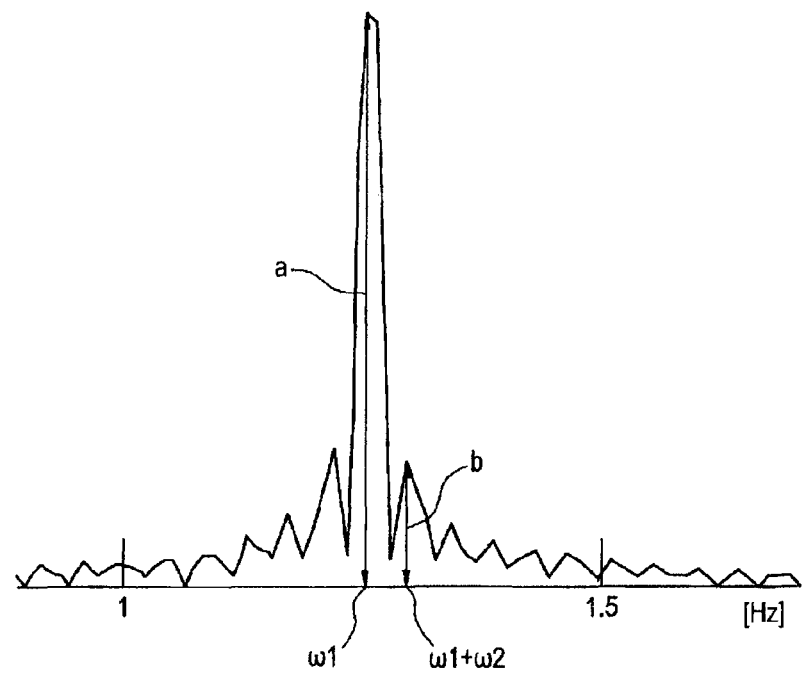

PULSE WAVE ANALYZING APPARATUS

TECHNICAL FIELD

The present invention relates to a pulse wave analyzing apparatus for obtaining the respiratory-induced variation of the arterial pressure.

BACKGROUND ART

The respiratory-induced variation of the arterial pressure is one of important indexes for knowing the circulatory dynamics of the cardiac function. For example, a method is known in which the respiratory-induced variation is invasively measured by inserting a catheter into a blood vessel. However, this method is invasively performed, and therefore an excessive burden is sometimes imposed on the subject. Moreover, an apparatus for performing such measurement is massively configured, and the measurement time period is often prolonged. Therefore, for example, Patent Literature 1 discloses a method in which the respiratory-induced variation of the arterial pressure is non-invasively obtained by blood pressure measurement using the oscillometric method.

CITATION LIST

Patent Literature

[PTL 1]
Japanese Patent Publication No. 2008-237882A

SUMMARY OF INVENTION

Technical Problem

In the method disclosed in Patent Literature 1, the respiratory-induced variation of the arterial pressure is obtained by using a pressure waveform which is acquired through a blood pressure cuff. In the method, however, noises are easily included in the measured pressure waveform by an external cause such as that the subject moves the body during measurement, or that a part of the body of the subject or the blood pressure cuff is contacted with an external object, and therefore it is sometimes difficult to accurately obtain the respiratory-induced variation. This problem may occur not only in the case where a blood pressure cuff is used, but also in the case where a pulse oximeter or another pulse wave sensor is used. That is, there is a problem in that, in the case where a pressure waveform is acquired by a non-invasive technique, the respiratory-induced variation is difficult due to noises to be accurately calculated.

Therefore, it is an object of the invention to provide a pulse wave analyzing apparatus in which, while reducing the burden imposed on the subject, an index value indicating the respiratory-induced variation of the arterial pressure can be accurately obtained.

Solution to Problem

In order to achieve the above object, one aspect that the invention can take is a pulse wave analyzing apparatus, the pulse wave analyzing apparatus comprising:
  an acquiring section which acquires a pulse wave that is non-invasively measured; and
  an analyzer which calculates data on a frequency axis by using the pulse wave, and which obtains an index value of a respiratory-induced variation based on the data on the frequency axis.

According to the pulse wave analyzing apparatus of the invention, while reducing the burden imposed on the subject, an index value indicating the respiratory-induced variation can be accurately obtained.

BRIEF DESCRIPTION OF DRAWINGS

FIG. 1 is a diagram of a pulse wave analyzing apparatus of an embodiment of the invention.

FIG. 2 is a flowchart illustrating the operation of a pulse wave analyzing apparatus of Embodiment 1.

FIG. 3A is a graph showing a cuff pressure applied to the subject.

FIG. 3B is a graph showing a pulse wave which is superimposed on the cuff pressure.

FIG. 4A is a graph in which the pulse wave shown in FIG. 3B is enlarged.

FIG. 4B is a graph showing the amplitude value of the pulse wave.

FIG. 5A is a graph showing the variation rate of the amplitude of a pulse wave

FIG. 5B is a graph in which the variation rate shown in FIG. 5A is frequency-analyzed.

FIG. 6A is a graph illustrating the reliability of the respiratory-induced variation.

FIG. 6B is a graph illustrating the reliability of the respiratory-induced variation.

FIG. 7 is a flowchart illustrating the operation of a pulse wave analyzing apparatus of Embodiment 2.

FIG. 8A is a graph showing a pulse wave which is superimposed on a cuff pressure.

FIG. 8B is a graph in which the pulse wave shown in FIG. 8A is frequency-analyzed.

FIG. 9A is a graph in which a part of the pulse wave shown in FIG. 8A is enlarged.

FIG. 9B is a graph in which a region E of a spectrum shown in FIG. 8B is enlarged.

DESCRIPTION OF EMBODIMENTS

Hereinafter, an example of an embodiment will be described in detail with reference to the drawings.

Embodiment 1

As shown in FIG. 1, a pulse wave analyzing apparatus 1 includes an acquiring section 11, an analyzer 12, a storing section 13, a controller 14, a displaying section 15, and a notifying section 16.

The pulse wave analyzing apparatus 1 is communicably connected to a measuring device A, and receives measurement data measured by the measuring device A.

The measuring device A is a device for non-invasively measuring a pulse wave of the subject. The embodiment uses the measuring device A including a cuff 21, a pressure controller 17, and a detector 18. In the embodiment, the pressure controller 17 and the detector 18 are incorporated in the pulse wave analyzing apparatus 1. The cuff 21 is attached to a portion of the subject from which the artery can be detected, such as an upper arm portion. The pressure controller 17 controls the pressure applied to the cuff 21, and the detector 18 detects the cuff pressure. The pressure applied to the cuff 21 is controlled so as to have a fixed value which is in a range that is equal to or lower than the diastole blood pressure of the subject, and that does not contain a pulse wave component of the vein, for example, from 40 to 50 mmHg. The cuff pressure is continuously detected for a predetermined time period (for example, one minute) by the detector 18. The pulse wave of the subject is superimposed on the detected cuff pressure, and the cuff pressure on which the pulse wave is superimposed is output (transmitted) from the measuring device A to the outside. The device for measuring the pulse wave is not limited to the measuring device A. For example, another sensor such as a pulse oximeter which is to be attached to the finger tip or ear lobe of the subject may be used.

The acquiring section 11 acquires the cuff pressure output from the measuring device A. Furthermore, the acquiring section 11 performs a signal process on the cuff pressure to acquire the pulse wave which is superimposed on the cuff pressure. The thus acquired pulse wave is configured by a plurality of unit pulse waves. A unit pulse wave means a unit of pulse wave corresponding to one heart beat. A plurality of unit pulse waves are contained in pulse wave data of the predetermined time period.

The analyzer 12 calculates the amplitude values of the unit pulse waves contained in the pulse wave, and the average value (hereinafter, referred to as the average amplitude value) of the amplitude values of the unit pulse waves. The analyzer 12 further calculates an amplitude ratio which is a ratio of the amplitude value of each unit pulse wave to the average amplitude value (hereinafter, the amplitude ratio is referred to as the variation rate of the amplitude of the pulse wave, or as the variation rate of the pulse wave). The analyzer 12 performs frequency analysis (for example, the Fourier transform) on the variation rate of the pulse wave, and converts time-axis data to frequency-axis data. The analyzer 12 further calculates an index value of the respiratory-induced variation of the arterial pressure from a frequency spectrum. Moreover, the analyzer 12 determines the reliability of the calculated index value of the respiratory-induced variation. Based on the calculated data, furthermore, the analyzer 12 produces a graph showing transitions of the data. As a frequency analysis technique, any technique may be used as far as it can take out frequency components. For example, the wavelet transform may be used.

The storing section 13 stores data such as: the cuff pressure acquired by the acquiring section 11; the pulse wave superimposed on the cuff pressure; the amplitude values of the unit pulse waves, and variation rate of the pulse wave which are calculated by the analyzer 12; the frequency spectrum; and results of the analyses.

The controller 14 causes graphs showing transitions of data, the index value of the respiratory-induced variation, the reliability thereof, and the like to be displayed on the displaying section 15. The controller 14 further causes, for example, a situation where an analysis result is abnormal, to be notified from the notifying section 16 by means of sound, light, or the like.

The displaying section 15 is configured by, for example, a touch-panel liquid crystal screen. The displaying section 15 is not always required to be disposed on the housing of the pulse wave analyzing apparatus 1, and may be configured on a tablet terminal which is formed in a separate housing, and which is carried by the doctor or the like. The notifying section 16 is configured by a speaker, an LED light, and the like.

Next, the operation of the pulse wave analyzing apparatus 1 will be described with reference to FIGS. 2 to 6B.

Firstly, the acquiring section 11 acquires the cuff pressure which is applied to the subject, and which is measured by the measuring device A (step S101, see FIG. 3A). In the example shown in see FIG. 3A, the cuff pressure which is maintained at about 45 mmHg that is equal to lower than the diastole blood pressure of the subject is acquired by the acquiring section 11 for about one minute.

Then, the acquiring section 11 filters the cuff pressure acquired in step S101 to acquire the pulse wave superimposed on the cuff pressure (step S102, see FIG. 3B).

Then, the analyzer 12 calculates the amplitude values of the unit pulse waves in the pulse wave acquired in step S102, and the average amplitude value of the unit pulse waves (step S103).

Specifically, the analyzer 12 calculates the amplitudes H of the unit pulse waves shown in FIG. 4A. FIG. 4B is a graph showing the temporal transition of the amplitude values of the unit pulse waves of FIG. 4A. From the graph of FIG. 4B, it is seen that the amplitude value of the pulse wave transits between about 0.70 mmHg and 0.76 mmHg. The analyzer 12 may be configured so that the analyzer predetermines a level range of the amplitude value, and, when an amplitude value outside the range is calculated, the corresponding pulse wave is excluded from analysis samples. Alternatively, the analyzer 12 may not exclude a pulse wave in which the amplitude value is outside the range, but may replace the amplitude value with one which is obtained by, for example, performing interpolation based on the amplitude values of several preceding and subsequent pulse waves, and then presumption.

Thereafter, the analyzer 12 calculates the variation rate of the pulse wave by dividing the amplitude values of the unit pulse waves by the average amplitude value which is calculated in step S103 (step S104, see FIG. 5A). In the example shown in FIG. 5A, the variation rate varies between about 0.95 and 1.035. In the graph, T indicates the respiratory cycle, and h indicates the amplitude of the variation rate in one respiration. Although, in the embodiment, the analyzer 12 performs the division of the amplitude values of the unit pulse waves by using the average amplitude value, the manner of the division is not limited to this. The division may be performed by using a value in which a ratio to the reference value can be calculated, such as the median amplitude value of the amplitudes of the unit pulse waves.

Thereafter, the analyzer 12 frequency-analyzes the variation rate of the pulse wave (step S105). Before performing the frequency analysis, preprocessing such as a process of removing the DC component, and spline interpolation is performed on the data of the variation rate of the pulse wave. As a result of the frequency analysis, the data of the variation rate which are time-axis data are converted to frequency-axis power spectrum data.

FIG. 5B is a graph showing a power spectrum which is obtained by frequency-analyzing the variation rate of the pulse wave shown in FIG. 5A.

Then, the analyzer 12 calculates an index value of the respiratory-induced variation based on the respiratory cycle of the subject and the power spectrum (step S106). In the case where an artificial respirator is connected to the subject, for example, the respiratory cycle of the subject can be acquired from control values of the artificial respirator. In the embodiment, the artificial respirator controls the respiratory cycle so as to be one respiration per 5 seconds (0.2 Hz). In the embodiment, therefore, the power value at 0.2 Hz in the graph of FIG. 5B is identified as the object power value which is to be used in the calculation of the respiratory-induced variation. The value of the square root of the identified object power value, i.e., that of the square root of the power value in the respiratory cycle is calculated as the index value of the respiratory-induced variation. This is based on the fact that the power value which is obtained by frequency-analyzing the variation rate of the pulse wave corresponds to the square of the variation rate of the amplitude of the pulse wave. The index value of the respiratory-induced variation is not limited to the value of the square root of the power value, and may be any index as far as it is possible to acquire a change of the amplitude value due to respiration. For example, the power value as it is may be used as the index value.

Alternatively, the configuration for identifying the respiratory cycle of the subject may be, for example, a configuration in which the analyzer 12 automatically reads and acquires control values of the artificial respirator, or that in which the doctor inputs information of the respiratory cycle from the outside in the analyzer 12. In the case where the pulse wave analyzing apparatus 1 (the analyzer 12) has a function which can measure the respiratory cycle (the measurement function of a so-called capnograph), a configuration in which the respiratory cycle is identified by the respiratory rate that is acquired by the function may be employed. Alternatively, a configuration may be employed in which a frequency range that can be usually expected as a respiratory cycle is predetermined, and a program that, for example, identifies a frequency at which the maximum power value is obtained in the frequency range, as the respiratory cycle of the subject is disposed.

Then, the analyzer 12 determines the reliability of the index value of the respiratory-induced variation which is calculated in step S106 (step S107). The reliability determination is performed based on the degree of the power value in a predetermined frequency band.

In the case where the respiration frequency of the subject is included in the range of 0.15 to 0.40 Hz, for example, ranges of from 0 to 0.15 Hz and from 0.40 Hz to the heart beat appearance frequency (in the embodiment, 1.25 Hz) are set as the predetermined frequency band. The sum of power values in the set frequency band, i.e., the area of the hatched regions B and C in the graph of FIG. 5B, and the sum of power values in the range of the respiration frequency, i.e., the area of the hatched region D are calculated. Then, it is determined that the power values in the predetermined frequency band are noise components, and the ratio of the area of B and C to that of D is calculated, whereby the reliability is determined.

For example, the determination is performed while using whether the area of B and that of C exceed a threshold or not, whether the area of D exceeds a threshold or not, whether the ratio of the area of B and C to that of D exceeds a threshold or not, and the like, as an index. In an example shown in FIG. 6A, noise components are large, and therefore the variation rate of the pulse wave is large with the result that, when the frequency analysis is performed, the power spectrum is as shown in FIG. 6B. In such a case, it is determined that the area of B and that of C exceed the threshold, and it is determined that the calculated value of the respiratory-induced variation has low reliability.

Of course, the reliability may be determined by using only the area of B or that of C. Alternatively, the reliability may be determined by using information indicating the degree by which the peak value (maximum value) of the region of B is larger (or which shows the value of a ratio of the peak value to that of the region of D). The peak value of the region of C may be used. The reliability may be determined by using both the peak values of the regions of B and C. The reliability determination may be performed by using only an area of the hatched regions B and C which is equal to or larger than a fixed value (for example, 0.005). As described above, the analyzer 12 may be configured so as to perform the reliability determination by using the power value in a predetermined frequency band.

Then, the controller 14 causes the data such as the index value of the respiratory-induced variation which is calculated in step S106, the reliability of the index value of the respiratory-induced variation which is determined in step S107, and the data of the power spectrum which is calculated in step S105, to be displayed on the screen of the displaying section 15 (step S108).

In the case where the calculated index value of the respiratory-induced variation exceeds a predetermined threshold, thereafter, the controller 14 controls the notifying section 16 so as to output an warning alarm or the like (step S109). In this way, a series of operations of the pulse wave analyzing apparatus 1 are ended.

The controller 14 may control the display of the index value of the respiratory-induced variation on the displaying section 15 in accordance with the value of the reliability (for example, the above-described ratio of the area of B and C to that of D, and the ratio of the peak value of the region of B to that of the region of D). In the case where the value of the reliability is compared with a predetermined threshold, and the reliability is determined to be low, for example, the controller 14 may change the display effect of the index value of the respiratory-induced variation as compared with that in the normal time (in the case where the reliability is determined to be high). For example, the display effect may be changed in the following manner: "in the case where the reliability is low, the index value of the respiratory-induced variation is not displayed"; "the index value of the respiratory-induced variation is displayed simultaneously with an alarm message (Measurement is not correct due to the influence of noises or the like.)"; "the index value of the respiratory-induced variation blinks"; or "the index value of the respiratory-induced variation is displayed in a color different from the usual color." In addition to the change of the display effect, an alarm may be sounded. When the display effect of the index value of the respiratory-induced variation is changed as described above, the user (mainly, the doctor or the nurse) can recognize that it is highly possible that the index value of the respiratory-induced variation of the subject cannot be correctly acquired. Therefore, the user can perform diagnosis or treatment while knowing also the correctness of the index value of the respiratory-induced variation. The controller 14 may display a trend graph showing transition of the value of the reliability.

For example, a method has been known in which the respiratory-induced variation is invasively measured by inserting a catheter into a blood vessel. In the method, by using a measured blood pressure waveform, the PPV (Pulse Pressure Variation) is obtained from following Exp. 1:

$$PPV=(H\max-H\min)/((H\max+H\min)/2)\times 100[\%] \qquad \text{(Exp. 1)}.$$

The respiratory-induced variation which is obtained from the expression is a value which is obtained by dividing the difference between the maximum amplitude (Hmax) of the pulse wave in one reciprocation and the minimum amplitude (Hmin), by the average of the maximum amplitude of the pulse wave and the minimum amplitude of the pulse wave, and indicates the variation rate of the amplitude level of the pulse wave in one reciprocation. The calculation is completed by computation on time-axis data, and obtains one variation rate per reciprocation.

In the above-described invasive method, the accuracy is high, but much trouble must be taken. Therefore, for example, a method in which the respiratory-induced variation is non-invasively measured by using a blood pressure cuff has been proposed. In the method, however, noises are easily included in the measured pressure waveform by an external cause, and, as compared with the invasive method, it is difficult to accurately measure the respiratory-induced variation.

In order to accurately obtain the index value of the respiratory-induced variation by a non-invasive method, the inventors have firstly studied the removal of noise components included in a pulse wave. The inventors have frequency-analyzed the variation rate of a pulse wave similarly with the embodiment, identified the frequency at which a peak of the power value appears, and produced a band-pass filter having a range of ±0.02 Hz of the identified frequency. For example, a band-pass filter Y that, in accordance with a frequency of 0.2 Hz at which a peak appeared, has characteristics of 0.18 to 0.22 Hz has been produced, a filtering process has been performed on the pulse wave by using the band-pass filter Y, and the index value of the respiratory-induced variation has been calculated from the pulse wave data obtained by the filtering process.

The correlation coefficient between the index value of the respiratory-induced variation calculated by performing the filtering process, and the respiratory-induced variation (true value) obtained by the above-described invasive method has been calculated. It has been noted that, even when such a filtering process is performed, the calculation accuracy of the respiratory-induced variation cannot be sufficiently enhanced.

By contrast, according to the pulse wave analyzing apparatus 1 of the embodiment, by using a pulse wave which is non-invasively acquired from the subject, the variation rate of the pulse wave is calculated, the calculated variation rate is frequency-analyzed, and the square root of the power value at the respiration frequency of the subject is obtained, whereby the index value of the respiratory-induced variation is calculated. That is, the data of the variation rate which are on the time axis of the pulse wave that is no-invasively measured are converted to frequency-axis power spectrum data, and the index value of the respiratory-induced variation is calculated from the power spectrum data, thereby performing a calculation corresponding to (Exp. 1) above for invasively obtaining PPV.

The correlation coefficient between the index value of the thus obtained respiratory-induced variation and the respiratory-induced variation (true value) obtained by an invasive method was calculated, and a high correlation was confirmed. This seems to be because, while noise components are eliminated by the frequency analysis from the pulse wave which was non-invasively acquired from the subject, a variation component related to the respiratory-induced variation can remain. In this way, the inventors have found that the index value of the respiratory-induced variation can be accurately obtained based on frequency-axis data.

Similarly with the technique of (Exp. 1) above for invasively obtaining the respiratory-induced variation, the amplitudes of unit pulse waves are divided by the average amplitude value, and therefore the index value of the respiratory-induced variation can be obtained with an accuracy which is similar to that of the invasive technique of (Exp. 1).

In the case where an artificial respirator is connected to the subject and the respiratory cycle of the subject is controlled, even when the setting of the respiratory cycle of the artificial respirator is changed, for example, the setting change is caused to be read by the analyzer 12, whereby an optimum object power value which is to be used in the calculation of the respiratory-induced variation can be always identified, and the index value of the respiratory-induced variation can be correctly obtained. Also in the case where the pulse wave analyzing apparatus 1 has a function of measuring the respiratory cycle, the index value of the respiratory-induced variation can be similarly obtained.

As shown in FIG. 5B, for example, the sum of power values of the area of B and C in the predetermined frequency band (0 to 0.15 Hz, 0.40 to 1.25 Hz), and the sum of power values of the area of D in the respiration frequency band (0.15 to 0.40 Hz) are obtained, whereby the reliability of the respiratory-induced variation can be correctly determined based on the ratio of the sums of the power values. Furthermore, the reliability of the respiratory-induced variation can be determined also depending on whether the area of B and that of C exceed a threshold or not.

Embodiment 2

Next, Embodiment 2 of the invention will be described. The portions which are configured in the same manner as Embodiment 1 are denoted by identical reference numerals, and their description is omitted. A pulse wave analyzing apparatus 1A of the embodiment is different from the pulse wave analyzing apparatus 1 of Embodiment 1 in which the variation rate of the pulse wave is frequency-analyzed, in that frequency analysis is performed without conducting calculations of obtaining the amplitude ratio and the like on the pulse wave acquired from the subject.

The operation of the pulse wave analyzing apparatus 1A will be described with reference to FIGS. 7 to 9B.

Firstly, the acquiring section 11 acquires the cuff pressure which is measured by the measuring device A (step S201). Then, the acquiring section 11 filters the cuff pressure acquired in step S201 to acquire the pulse wave superimposed on the cuff pressure (step S202, see FIG. 8A).

Then, an analyzer 12A performs frequency analysis (the Fourier transform) on the pulse wave acquired in step S202 (step S203). When the frequency analysis is to be performed, a process of removing the DC component may be performed on the signal of the pulse wave. As a result of the frequency analysis, the time-axis data of the pulse wave are converted to frequency-axis power spectrum data (see FIG. 8B). In the example shown in FIG. 8B, it is seen that frequency components are largely distributed in the vicinity of 1.25 Hz.

Then, the analyzer 12A identifies the fundamental frequency of the pulse wave, and the frequencies of the sideband waves, and extracts the power value at the fundamental frequency of the pulse wave, and the power values at the frequencies of the sideband waves from the data which are frequency-analyzed (step S204). The fundamental frequency of the pulse wave is measured from the pulse wave acquired in step S202. The frequencies of the sideband waves are calculated based on the fundamental frequency of the pulse wave and the respiratory cycle of the subject.

FIG. 9A is an enlarged view showing a part of the pulse wave of FIG. 8A. In the embodiment, the fundamental frequency of the pulse wave is measured as about 1.25 Hz.

In FIG. 8B and FIG. 9B, $\omega 1$ indicates the fundamental frequency of the pulse wave, and $\omega 2$ indicates the frequency of the respiratory cycle of the subject. The powers of the sideband waves symmetrically appear on the both sides of the fundamental frequency $\omega 1$ of the pulse wave, respectively. The frequencies of the sideband waves are indicated by $\omega 1 \pm \omega 2$ [Hz]. In the case where, similarly with Embodiment 1 above, the respiratory cycle of the subject is controlled to 5 seconds (0.2 Hz) by an artificial respirator, the frequencies of the sideband waves are calculated as ($\omega 1-\omega 2$ and $\omega 1+\omega 2$), respectively.

FIG. 9B is a view in which a region E of FIG. 8B is enlarged. The power value a at the fundamental frequency ($\omega 1$) of the pulse wave, and the power value b at the frequency ($\omega 2$) of the sideband wave are extracted by the analyzer 12A.

Then, the analyzer 12A obtains the square root of the power value b at the frequency of the sideband wave, and that of the power value a at the fundamental frequency of the pulse wave, and calculates the value which is obtained by dividing the square root of the power value b by that of the power value a, as the index value of the respiratory-induced variation (step S205). This is performed based on the finding by the inventors that, in the case where a pulse wave is frequency-analyzed, the power values of the sideband waves appearing on the both sides of the power value of the fundamental frequency of the pulse wave indicate the power value of a variation component superimposed on the fundamental frequency of the pulse wave.

Then, the controller 14 controls the displaying section 15 so as to display data such as the index value of the respiratory-induced variation and the produced graphs thereon (step S206). If the value of the respiratory-induced variation is determined to be abnormal, the controller 14 controls the notifying section 16 so as to output an warning alarm or the like (step S207).

The pulse wave analyzing apparatus 1A of the embodiment calculates the value of the square root (indicating the level of a variation component) of the power value at the frequency of the sideband wave with respect to the square root (indicating the level of the amplitude of the pulse wave) of the power value at the fundamental frequency of the pulse wave, thereby performing a calculation corresponding to a process of obtaining the respiratory-induced variation.

Also in the technique, noises contained in the pulse wave can be eliminated, and the index value of the respiratory-induced variation can be accurately obtained.

The invention is not limited to the above-described embodiments, and may be adequately subjected to modifications, improvements, and the like. In addition, the materials, shapes, dimensions, values, forms, numbers, places, and the like of the components of the above-described embodiments are arbitrary and not limited insofar as the invention is achieved.

For example, the pulse wave analyzing apparatus may be disposed as a part of a bedside monitor, a blood pressure measuring apparatus, an artificial respirator, an anesthesia apparatus, or the like.

The present application is based on Japanese Patent Application No. 2014-251022 filed on Dec. 11, 2014, the contents of which are hereby incorporated by reference.

The invention claimed is:

1. A pulse wave analyzing apparatus comprising:
an acquiring section which acquires a pulse wave that is non-invasively measured during a respiratory cycle of a subject; and
an analyzer which calculates an amplitude of the pulse wave, calculates a variation rate of the amplitude of the pulse wave, frequency-analyzes the variation rate to provide frequency data, and obtains an index value of a respiratory-induced variation of the pulse wave by calculating a power value of the frequency data.

2. The pulse wave analyzing apparatus according to claim 1, wherein the analyzer calculates a square root of the power value, thereby obtaining the index value of the respiratory-induced variation.

3. The pulse wave analyzing apparatus according to claim 2, wherein the analyzer identifies a frequency of the frequency data that is an object from which the square root of the power value is to be calculated, based on information related to the previously acquired respiratory cycle of the subject.

4. The pulse wave analyzing apparatus according to claim 1, wherein the variation rate is calculated by dividing amplitude values of unit pulse waves contained in the pulse wave, by an average amplitude value of the unit pulse waves.

5. The pulse wave analyzing apparatus according to claim 1, wherein the analyzer determines a reliability of the index value of the respiratory-induced variation, based on a power value of a predetermined frequency.

6. The pulse wave analyzing apparatus according to claim 1, wherein the analyzer obtains the index value of the respiratory-induced variation by calculating a square root of a ratio of a power value of a sideband wave to a power value of a fundamental frequency.

7. The pulse wave analyzing apparatus according to claim 6, wherein the analyzer identifies a frequency of the sideband wave based on information related to a previously acquired respiratory cycle of the subject.

8. The pulse wave analyzing apparatus according to claim 7, wherein the respiratory cycle is calculated by using information of a respiratory rate which is controlled by a respirator.

9. The pulse wave analyzing apparatus according to claim 5, wherein:
the apparatus further includes a controller which causes the index value of the respiratory-induced variation to be displayed on a displaying section, and
in accordance with the reliability of the index value of respiratory-induced variation, the controller controls the display of the index value of the respiratory-induced variation.

10. The pulse wave analyzing apparatus according to claim 3, wherein the respiratory cycle is calculated by using information of a respiratory rate which is controlled by a respirator.

11. The pulse wave analyzing apparatus according to claim 1, wherein the index value of the respiratory-induced variation is calculated based on only the power value.

* * * * *